United States Patent [19]

Jorgensen

[11] 4,288,472
[45] Sep. 8, 1981

[54] METHOD OF PRODUCING UNIFORM SYNTHETIC RESIN COATINGS ON WORKING CASTS FOR DENTAL APPLICATIONS

[75] Inventor: Knud D. Jorgensen, Copenhagen, Denmark

[73] Assignee: Etablissement Dentaire Ivoclar, Munich, Fed. Rep. of Germany

[21] Appl. No.: 101,985

[22] Filed: Dec. 7, 1979

[30] Foreign Application Priority Data

Dec. 7, 1978 [DE] Fed. Rep. of Germany ....... 2852984

[51] Int. Cl.³ ............................................. A61C 13/00
[52] U.S. Cl. ........................................ 427/133; 427/2; 427/135; 264/19; 264/16; 433/213; 260/998.11
[58] Field of Search ....................... 433/213, 218, 219; 427/2, 133, 135; 264/19, 16; 260/998.11

[56] References Cited

U.S. PATENT DOCUMENTS 3,431,330  3/1969  Cornell ........................... 260/998.11

Primary Examiner—Sam Silverberg
Attorney, Agent, or Firm—Sprung, Felfe, Horn, Lynch & Kramer

[57] ABSTRACT

A method of producing a uniform synthetic coating on a working cast for dental applications which comprises:
(A) applying to or introducing in said working cast a first catalyst component which, when initiated by a second catalyst component, effects polymerization of a polymerizable composition;
(B) thereafter applying to said working cast said second catalyst component and a polymerizable composition which, when polymerized, forms a resin; and
(C) thereafter effecting polymerization of said polymerizable composition to form a film.

9 Claims, 2 Drawing Figures

METHOD OF PRODUCING UNIFORM SYNTHETIC RESIN COATINGS ON WORKING CASTS FOR DENTAL APPLICATIONS

The invention relates to a method of producing uniform synthetic resin coatings on working casts for dental applications, and in particular on the roots of teeth or in cavities for inlays.

The production of a cast crown starts with preparation of the root in the mouth, followed by making an impression and pouring suitable materials such as cements, synthetic resins, gypsum, metals, ceramics, etc., into the impression. The working cast so produced, the so-called root model, corresponds exactly to the root prepared by the dentist, and the further handling is then taken over by the dental technician. A wax layer is molded onto the working cast, stripped therefrom, and invested with a refractory material. The finished cast crown is obtained by pouring suitable dental alloys into the mold.

Placement of the crown in the mouth is attended by difficulties stemming from the geometric relationships. To mount the crown on the ground-down root in the mouth, a phosphate or carboxylate cement, for example, is used. Because of the particle size of the powder used, the thickness of the thinnest practicable cement layer ranges from 5 to 30$\mu$. Now since the ground-down root is conical and the crown is provided with surfaces which are parallel thereto, too close a fit between crown and root, or too small a crown, will result in an occlusal discrepancy, that is to say, the crown will be raised in the direction of the occlusion surface as a function of the thickness of the cement layer and of the angle of inclination of the root. This is why the necessary space for the cement layer must be allowed for from the outset, that is to say, the fit must be loose. This is accomplished by the use of lacquers which are brushed onto the working cast before the crown is molded from the wax. However, expanding materials are also used for filling the impressions, and still other methods of applying a spacing layer are known.

All these methods have the drawback that they do not permit a perfectly uniform thickness of the spacer film to be obtained. Particularly troublesome are the brushed-on lacquers. Here the film thickness varies a great deal, and since the edges and corners of the prepared root are markedly rounded anyway, said displacements in the direction of the occlusion surface and other inaccuracies occur when crowns made from such molds are cemented in place. In the final analysis, the nonuniform film thickness also accounts for the poor fit, coupled with poor marginal seating. The liquid of the oral cavity thus is better able to dissolve the cement used for bonding, and this leads to secondary caries. The same problems are encountered in the making of inlays.

The invention seeks to remedy these drawbacks and to provide synthetic resin coatings of uniform film thickness with a view to improving the accuracy of fit and the proper seating of dental restorations.

The object of the invention thus is a method of the type outlined above wherein a catalyst is applied to or introduced in the working cast, a polymerizable synthetic resin incorporating a second catalyst adapted to cure, together with the first catalyst, the polymerizable resin is applied to the working cast so treated, and the polymerizable resin is allowed to cure in the form of a thin film. The film thickness obtained by this method may be as high as 100$\mu$; however, it preferably ranges from 5 to 50$\mu$, and generally from 5 to 30$\mu$.

The first catalyst may be applied to or introduced in the working cast by any desired technique, the preferred techniques being dipping, brushing, spraying, and dropping. For this purpose, the first catalyst may be dispersed in a liquid vehicle. Preferably it is dissolved in a solvent and applied to the working cast in the form of a solution. After the solvent has evaporated, a uniform layer of the first catalyst remains on the working cast. However, the first catalyst may also be added directly to the material of which the working cast is made, in which case it may likewise be dissolved or dispersed in a suitable vehicle.

The synthetic resin layer, which hereinafter will be referred to also as molding film, is preferably formed by a polymerizable synthetic resin to which the second catalyst has been added prior to curing. After the first catalyst has been applied to the working cast, the molding film can be applied to it in the same manner. Preferably, however, the molding film is applied by dipping. Techniques which assure uniform deposition of the polymerizable resin are preferred. The thickness of the resin film produced depends on the concentration of the catalysts used, on the nature of these catalysts, and on the length of time during which the two catalysts are able to interact.

In accordance with a preferred embodiment of the invention, excess synthetic resin which has not cured or polymerized is removed with a solvent such as alcohol and the remaining resin film is contacted once more with the first catalyst. The latter again is preferably present in the form of a solution which may be deposited on the remaining resin film by dipping, brushing, spraying or dropping. In this way, thorough curing of the spacer film and a perfectly uniform film thickness are obtained.

The effect underlying the method in accordance with the invention may be explained by the fact that the first catalyst diffuses from the surface of the working cast into the layer of polymerizable synthetic resin and together with the second catalyst produces immediately the polymerization of a thin film. Since the diffusion of the first catalyst from the working-cast surface proceeds uniformly and independently of the dimensions and shape of the working cast, a uniform film thickness results. The film thickness is practically constant also at the edges and in the corners.

Suited for production of the molding film are preferably cold-curing polymerizable synthetic resins as used in dentistry, and preferably acrylates or methacrylates. Particularly well suited is the reaction product of bisphenol A and glycidyl methacrylate, hereinafter called bis-GMA, which may be used together with other diluting monomers on an acrylate or methacrylate basis, for example, or together with nonpolymerizing solvents or diluents. Other monomers suited for production of the synthetic resin layer are the mono-, di- and polyfunctional acrylates and methacrylates, such as methyl methacrylate, ethylene glycol dimethylacrylate, triethylene glycol dimethacrylate and trimethylolpropane trimethacrylate. Urethane acrylates or methacrylates may also be used to good advantage. These may be reaction products of organic isocyanates with polymerizable acrylic acid esters having at least one hydroxy group. Examples of such acrylates are the hydroxyethyl and hydroxypropyl acrylates and methacrylates, while the isocyanate may be toluylene or hexamethylene diisocyanate. The polymerizable acrylates or methacrylates may be used alone or as mixtures. This will depend both on the viscosity of the monomer and on the technique chosen for application of the monomer.

The method lends itself to use with all monomers or mixtures thereof which are polymerizable and which as such or as solutions have a viscosity not greater than about 3 Pa·s (at 20° C.). The viscosity of these monomers, monomeric mixtures or solutions should preferably not exceed 2 Pa·s, a particularly appropriate upper limit being about 1 Pa·s.

Suitable materials for the production of working casts are, in particular, the various grades of gypsum, such as plaster of Paris or special plaster of Paris; however, synthetic resins, cements or low-melting dental alloys may also be used to advantage. Any molding material is suited which is adapted to adsorb the first catalyst on its surface without reacting with it. The adhesion of the first catalyst to the working cast may be improved by the addition of a bonding agent to the catalyst solution.

In dentistry, so-called redox systems are employed for the polymerization of cold-curing synthetic resins. The polymerization catalysts used are mainly organic peroxides. Rapid decomposition of the peroxide is brought about by the use of a second catalyst, the activator, which results in the formation of free radicals which initiate the polymerization. The most common peroxide catalysts are benzoyl peroxide, 2,4-dichlorobenzoyl peroxide, 4-chlorobenzoyl peroxide, lauroyl peroxide, 6-butyl peroxide, methyl ethyl ketone peroxide and cyclohexanone peroxide. Other catalysts consist of a combination of peroxide, a sulfinic acid or sulfinic acid derivative, and traces of copper salts. These catalysts are preferably used in amounts of not more than about 20 weight percent. The preferred range is 10 to 20 weight percent, and more particularly 1 to 10 weight percent, based on the weight of the particular vehicle (solvent or dispersant).

The second catalyst serving as activator is preferably an amine such as an N,N-dialkylaniline or an N,N-dialkyltoluidine. Preferred compounds are N,N-dimethyl-p-toluidine, N,N-di-(2-hydroxyethyl)-p-toluidine, diethylaniline, and N,N-dimethylaniline. Cobalt compounds are also suited. These are used so that the synthetic resin contains from 0.01 to 1 weight percent cobalt (calculated as metal). Another metal catalyst is vanadium salt (for example, vanadyl tosylate), which is used with peroxy esters, and in particular with tert-butylperoctoate. These catalysts are preferably used in amounts of not more than about 20 weight percent, the preferred range being 5 to 10 weight percent, and more particularly 0.5 to 5 weight percent. The amounts specified again are based on the weight of the vehicle, in this case, the polymerizable monomer or mixture of monomers or the solution of the monomer or mixture of monomers.

In practice, the two types of catalyst must be stored separately as otherwise polymerization will set in at once. In accordance with the invention, the interaction between the two catalysts occurs in a thin resin layer on the surface of the working cast. In principle it is immaterial whether the peroxide, for example, is present on the surface of the working cast; but in that case the amine must be contained in the polymerizable synthetic resin, and vice versa.

The first catalyst is preferably deposited on the surface of the working cast. This may be done with or without the use of solvents such as acetone, alcohol, chloroform or methylene chloride. If necessary, bonding agents with good adhesion to smooth surfaces may be used for the catalyst. Moreover, the molding material may also be mixed with a catalyst, which, however, must not react with the molding material as otherwise there will be no diffusion from the surface of the working cast into the synthetic resin. The organic peroxides are preferably dissolved in a solvent and the solution is applied to the working cast. The amine is then contained in the polymerizable synthetic resin or in a solution thereof.

EXAMPLES

EXAMPLE 1

Figure 1:
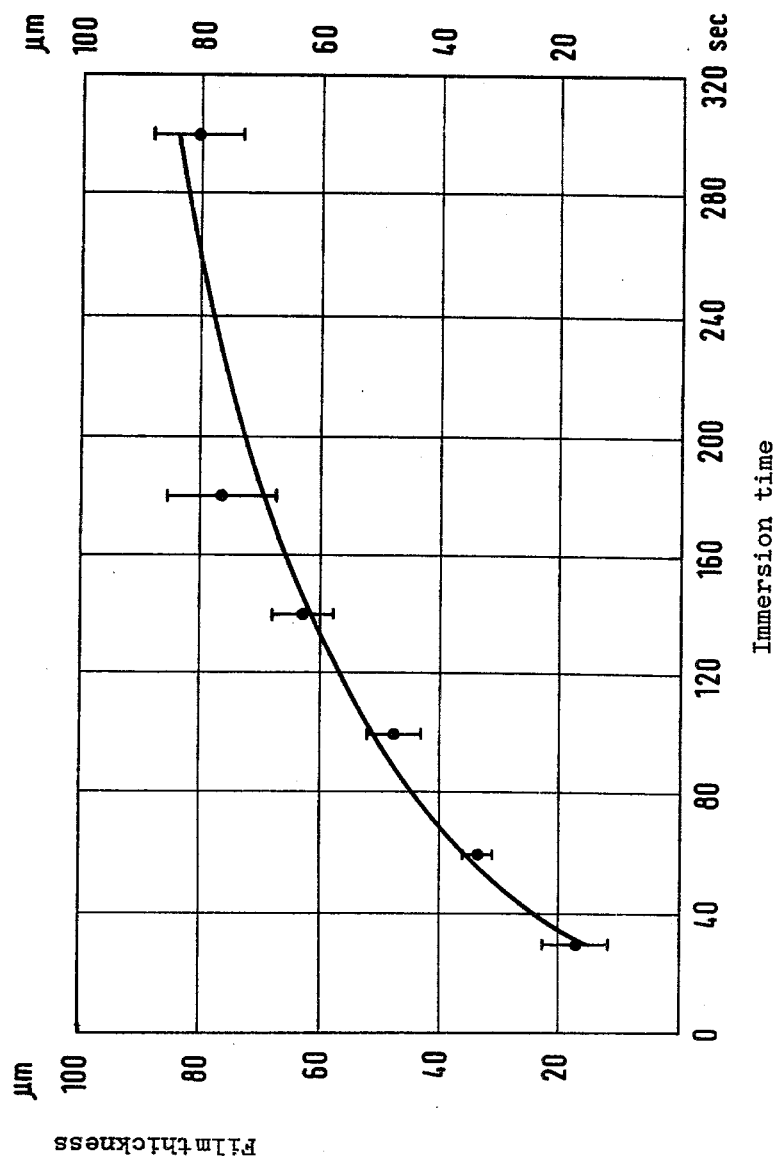
FIGS. 1 and 2 annexed plot, respectively, film thickness against immersion time (FIG. 1) and film thickness against peroxide concentration (FIG. 2).

A solution was prepared from 90 wt. % acetone and 10 wt. % benzoyl peroxide. The working cast used was a model of a root of the tooth, made of plaster of Paris which had been stirred in a vacuum. The root model was immersed for about 15 seconds in the benzoyl peroxide/acetone solution (first catalyst) and then air-dried for 5 minutes. A monomeric mixture composed of 47 wt. % bis-GMA and 51 wt. % triethylene glycol dimethacrylate and containing, moreover, 2 wt. % N,N-diethanol-p-toluidine as second catalyst was prepared, and the treated root model was then immersed in it. After a certain immersion time, the model was wiped with acetone. A uniform, thin coating was obtained. The film thickness was measured with a microscope at nine test points. Plotted in FIG. 1 is the film thickness as a function of the time of immersion of the root model in the monomeric mixture.

For comparison, no catalyst was deposited on the working cast but 1.0 wt. % benzoyl peroxide was added to the same mixture of monomer and amine. This mixture was then applied to the root model with a brush. Measurements showed that the film thickness was nonuniform, especially at the edges and in the corners.

EXAMPLE 2

A solution of 10 wt. % benzoyl peroxide in chloroform (first catalyst) was prepared and sprayed with an atomizer onto a root model made of gypsum. The monomeric mixture contained 59 wt. % bis-GMA, 19 wt. % triethylene glycol dimethacrylate and 20 wt. % bisphenol A dimethacrylate to which 2 wt. % N,N-dimethyl-p-toluidine (second catalyst) had been added. The monomeric mixture was likewise sprayed evenly but in excess onto the root model with an atomizer. The root model so treated was then allowed to stand for 3 minutes at about 22° C. It was found that except for a thin film the excess monomer had not polymerized even after that time, when it was washed off with ethanol. Measurement of the film showed that it had a thickness of 75μ. No significant variations in film thickness were observed.

EXAMPLE 3

The procedures according to Examples 1 and 2 were repeated, except that in place of the peroxide solution (first catalyst), a 2% amine solution (N,N-dimethyl-p-toluidine) was applied to the working cast. The amine in the monomeric mixture was replaced with 2.5 wt. % benzoyl peroxide. Comparable film thicknesses were obtained.

EXAMPLE 4

A root model was made from a bismuth-tin alloy. Nitrocellulose was then dissolved in ethyl acetate and 10 wt. % benzoyl peroxide was added to the solution. The root model was immersed for 30 seconds in the solution and then dried. The root model so treated was then immersed for 20 seconds in ethylene glycol dimethacrylate to which 5 wt. % diethanol-p-toluidine had been added. After 10 minutes, excess unpolymerized monomer was washed off with ethanol and the root model was immersed for 10 seconds in the peroxide solution according to Example 1. After 20 minutes, the film thickness was measured. A very hard, uniform, thin film about 30μ thick was obtained.

EXAMPLE 5

Figure 2:
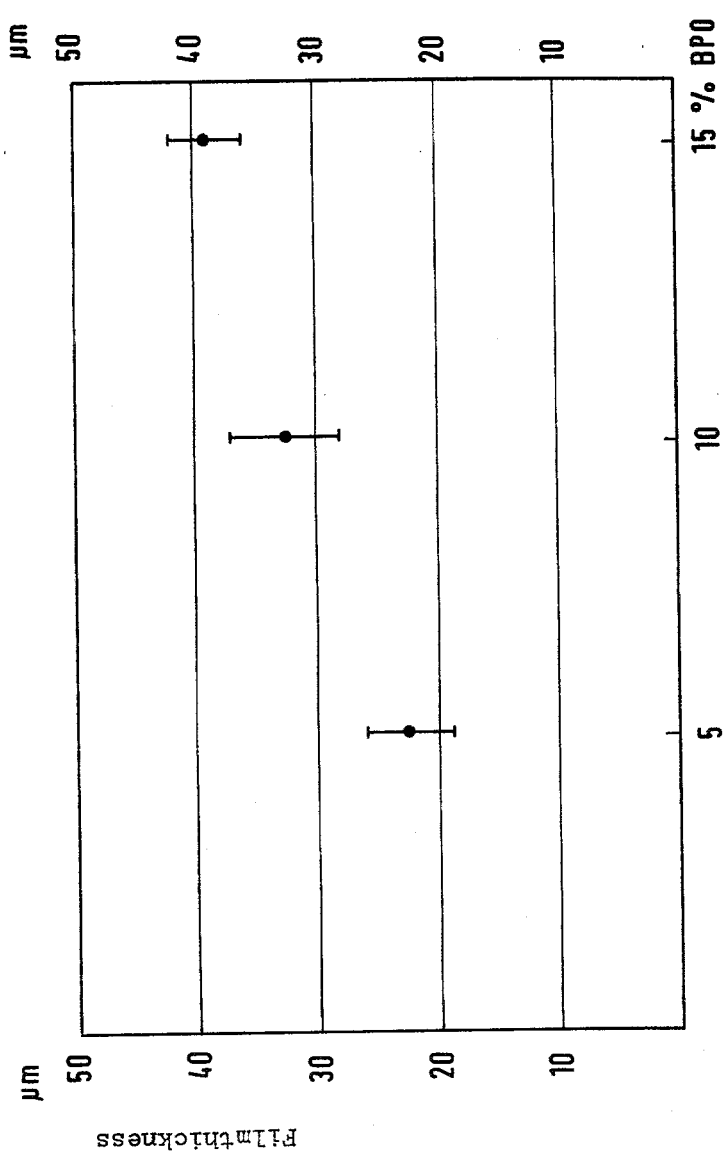

The procedure of Example 1 was repeated, except that the concentration of the benzoyl peroxide solution was varied. It was found that the film thickness is somewhat dependent on the peroxide concentration. (See FIG. 2.)

EXAMPLE 6

A plaster of Paris mold was used for an inlay. The walls of the cavity of the mold were brush-coated with the 10 wt. % benzoyl peroxide solution of Example 2. The monomeric mixture was composed of 10 wt. % methyl methacrylate, 40 wt. % bis-GMA, 45 wt. % triethylene glycol dimethacrylate, and 5 wt. % dimethyl-p-toluidine. The mold was immersed for 20 seconds in the monomeric mixture, then removed therefrom and washed with methanol. The measured film thickness was uniform. Most importantly, the rounded transition between wall and bottom of the cavity was less pronounced than in the comparative molds made by the conventional method.

EXAMPLE 7

A root model made of dental plaster was immersed for 30 seconds in a 2% benzoyl peroxide/acetone solution. The root was dried and immersed for 20 seconds in triethylene glycol dimethacrylate to which 2% dimethyl-p-toluidine had been added. The root was then rinsed for 1 minute in the peroxide/acetone solution.

The very hard film was of uniform thickness.

EXAMPLE 8

The root model was made from a polyester resin (Roskydal A 500 of Bayer). An 18% nitrocellulose/ethyl acetate solution was prepared and 5% benzoyl peroxide was added to it. This mixture was applied to the root model with a brush and then dried for 10 minutes. The model was then immersed for about 30 seconds in a mixture of 97% ethylene glycol dimethacrylate and 3% dimethyl-p-toluidine and rinsed with acetone.

The film was found to be of uniform thickness.

EXAMPLE 9

The procedure of Example 8 was repeated, except that dimethyl-p-toluidine was used in place of benzoyl peroxide. The film thicknesses measured were uniform.

What is claimed is:

1. A method of producing a uniform synthetic resin coating on a working cast for dental applications which comprises:
    (A) applying to or introducing in said working cast a first catalyst component which when initiated by a second catalyst component effects polymerization of a polymerizable composition;
    (B) thereafter applying to said working cast a composition comprising said second catalyst component and a polymerizable composition which when polymerized forms said resin; and
    (C) thereafter effecting polymerization of said polymerizable composition to form a film.

2. A method according to claim 1 wherein the first catalyst component is applied to or introduced in the working cast by dipping, brushing, spraying, or dropping.

3. A method according to claim 1 wherein the first catalyst component is applied to the working cast in the form of a solution.

4. A method according to claim 1 wherein the first catalyst component is added directly to the material of which the working cast is made.

5. A method according to claim 1 wherein an organic peroxide is used as the first catalyst component and an amine as the second catalyst component, or vice versa.

6. A method according to claim 1 wherein a polymerizable synthetic resin or a solution thereof having a viscosity of not more than about 3 PA.s is used as the polymerizable composition.

7. A method according to claim 6 wherein a resin which has not cured is removed with a solvent.

8. A method according to claim 1 wherein the catalysts are present in vehicles therefor and the catalysts are used in amounts of not more than about 20 weight percent, based on the weight of the respective vehicles.

9. A method according to claim 6 wherein resin which has not cured is removed with a solvent and the resin layer which remains is contacted once more with the first catalyst.

* * * * *

UNITED STATES PATENT AND TRADEMARK OFFICE

CERTIFICATE OF CORRECTION

PATENT NO. : 4,288,472
DATED : Sep. 8, 1981
INVENTOR(S) : Knud D. Jorgensen

It is certified that error appears in the above-identified patent and that said Letters Patent are hereby corrected as shown below:

Title Page   Delete "Munich, Fed. Rep. of Germany"
Assignment   and insert --Schaan, Liechtenstein--.

Signed and Sealed this

Eleventh Day of May 1982

[SEAL]

Attest:

GERALD J. MOSSINGHOFF

*Attesting Officer*   *Commissioner of Patents and Trademarks*